United States Patent [19]

Yagi

[11] Patent Number: 4,502,937

[45] Date of Patent: Mar. 5, 1985

[54] OPTICAL FIBER JOINT TYPE ION-CONCENTRATION MEASUREMENT APPARATUS

[75] Inventor: Taizo Yagi, Kyoto, Japan

[73] Assignee: Horiba, Ltd., Kyoto, Japan

[21] Appl. No.: 528,985

[22] Filed: Sep. 2, 1983

[30] Foreign Application Priority Data

Sep. 17, 1982 [JP] Japan ............... 57-162870

[51] Int. Cl.³ ................................. G01N 27/50
[52] U.S. Cl. .................... 204/406; 204/416;
307/252 F; 307/311; 315/149; 315/227 R;
324/96; 324/425; 324/438; 455/613
[58] Field of Search ............ 307/252 F, 311;
204/406, 416, 417, 418, 419, 420, 433; 324/425,
438, 96; 455/613; 315/149, 227 R, 227 A;
332/7.51

[56] References Cited

U.S. PATENT DOCUMENTS

| 4,029,976 | 6/1977 | Fish et al. ............... 307/311 |
| 4,218,746 | 8/1980 | Koshiishi ............... 364/571 |
| 4,290,146 | 9/1981 | Adolfsson et al. ............... 455/612 |
| 4,316,141 | 2/1982 | Adolfsson et al. ............... 324/96 |

Primary Examiner—G. L. Kaplan
Attorney, Agent, or Firm—Wenderoth, Lind & Ponack

[57] ABSTRACT

An optical fiber joint type ion-concentration measurement apparatus in which electrical signals which are detected by an ion selective electrode are transformed into optical signals which are transmitted to a receiving side of the apparatus by means of optical fibers. The detected signals from the electrode are frequency modulated by a voltage/frequency converter and the output of the voltage/frequency converter is used to control an electronic switch. The electronic switch controls a series circuit including a power source and a charging-discharging capacitor and a light emitting diode. The frequency modulated transformed detected signals therefore cause the light emitting diode to emit optical signals which are then transmitted by means of optical fibers. On the receiving end of the apparatus, the optical signals are transformed into electrical signals by a photo diode and then demodulated by a frequency/voltage converter to reproduce the original detected signals from the ion selective electrode.

4 Claims, 5 Drawing Figures

FREQUENCY/VOLTAGE CONVERTER

4,502,937

OPTICAL FIBER JOINT TYPE ION-CONCENTRATION MEASUREMENT APPARATUS

BACKGROUND OF THE INVENTION

1. Field of the Invention

The present invention relates to an optical fiber joint type ion-concentration measurement apparatus in which electrical signals which are detected by an ion selective electrode are transformed into optical signals which are transmitted to a receiving side of the apparatus by means of optical fibers.

2. Description of the Prior Art

An optical fiber joint type ion-concentration measurement apparatus of this kind has an advantage in that measurement errors due to disturbances and ground loop voltages can be significantly reduced in comparison to that of apparatus in which the transmitting side is connected to the receiving side by electrical cables.

However, in the conventional optical fiber joint type ion-concentration measurement apparatus, since the signals detected by an ion electrode are either amplified and used as is or the amplified signals are modulated in frequency through a voltage/frequency converter and used to cause an LED (Light Emitting Diode) to emit light, an extremely large electrical power consumption is needed and many problems must be solved in order to use them practically. That is to say, since a large consumption of electrical power is required, it is necessary to use a large-sized battery at the transmitting side or to connect the transmitting side to the receiving side by means of a power supply cable. In the former method, since the transmitting side apparatus becomes large-sized and heavy, it is difficult to carry about. In the latter method, it is not worthwhile to use an optical fiber joint type ion-concentration measurement apparatus since the advantages thereof are lost by the use of the power supply cable. At present, the apparatus, which use liquid crystal devices having a low power consumption instead of the LED devices are being proposed. However, since liquid crystal devices do not emit light by themselves but merely change the transmission of light, it is necessary to transmit the light to be irradiated to the liquid crystal devices from the receiving side, whereby the apparatus using such liquid crystal devices have disadvantages in that one more optical fiber is required and the circuit of the transmitting side is complicated in construction.

SUMMARY OF THE INVENTION

In respect of the above described points, the present invention provides an improved optical fiber joint type ion-concentration measurement apparatus in which LED devices, which emit light by themselves, are used, said LED devices being able to be driven by very small amounts of electrical power, and, in spite of it, the signals detected by an ion selective electrode can be transmitted to the receiving side with a high fidelity. The optical fiber joint type ion-concentration measurement apparatus according to the present invention comprises a transmitting side consisting of an ion selective electrode, a voltage/frequency converter for frequency modulating the signals detected by said ion selective electrode, a switch means which is switched on or off by the signals output from said converter, an LED device which is connected in series with said switch means, a charging circuit including a battery, and a charging-discharging capacitor having a series circuit consisting of said switch means and said LED device as a discharging circuit, wherein an electric charge which is accumulated in said capacitor is discharged when said switch means is switched on so as to cause said LED device to emit light, and the emitted light is transmitted to the receiving side by means of optical fibers.

BRIEF DESCRIPTION OF THE DRAWINGS

The drawings show the preferred embodiment of the present invention, in which.

DESCRIPTION OF THE PREFERRED EMBODIMENT

Figure 1:
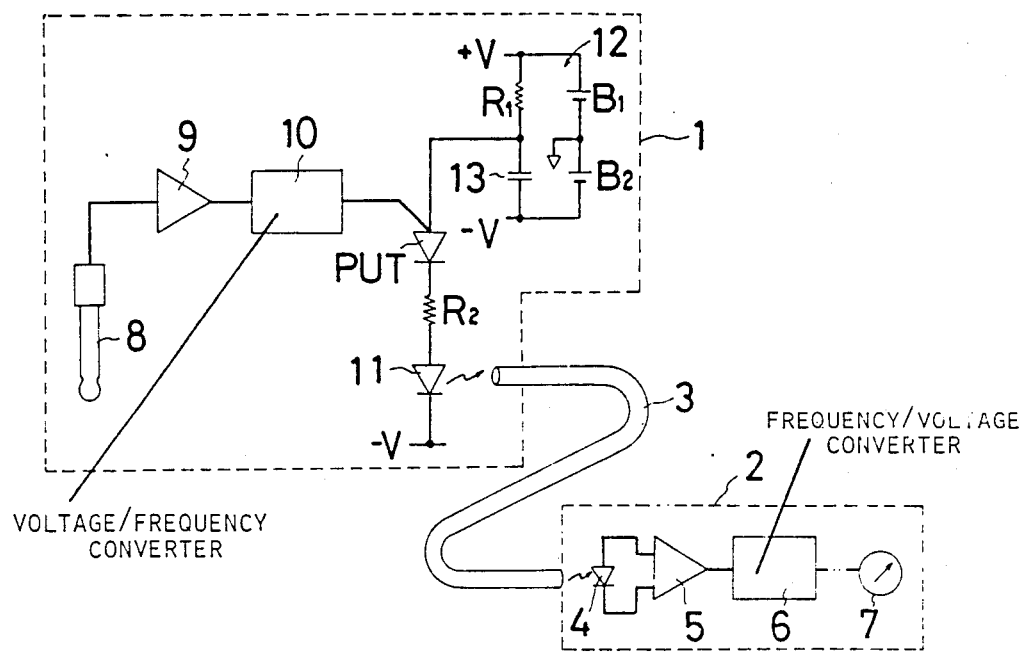
FIG. 1 is a schematic diagram of a basic configuration of the present invention.

The preferred embodiment of the present invention will be now described with reference to the drawings. Referring now to FIG. 1 showing the basic construction of the present invention, numeral 1 denotes the transmitting side; numeral 2 denotes the receiving side, and numeral 3 denotes an optical fiber for transmitting light from the transmitting side 1 to the receiving side 2. The receiving side 2 consists of a light receiving element 4, an amplifier 5, a frequency/voltage converter 6 and an indicating meter 7. The transmitting side 1 consists of an ion selective electrode 8, an amplifier 9 for amplifying signals detected by the ion selective electrode 8, a voltage/frequency converter 10 for frequency modulating signals output by the amplifier 9, a switch means, e.g., a PUT, which is switched on or off by the signals output by the voltage/frequency converter 10, an LED 11 which is connected in series with the PUT, a charging circuit 12 including batteries $B_1$ and $B_2$, and a charging-discharging capacitor 13 having a series circuit which consists of the PUT and the LED 11 and which is used as a discharging circuit. $R_1$ is an electrical resistance used for adjusting the charging current, and $R_2$ is an electrical resistance used for adjusting the discharging current. $R_1$ is preferably selected so as to be as large as possible with the object of reducing the electrical power consumption and $R_2$ is preferably selected so as to be as small as possible with the object of increasing the illuminating power of the LED.

According to the above described construction, the detecting signals which are generated by the ion selective electrode 8 are fed to the voltage/frequency converter 10 through the amplifier 9, where they are frequency modulated. The PUT is switched on or off with the same frequency as the frequency modulated signals. When the PUT is switched off, the capacitor 13 is charged by the charging circuit 12, and when the PUT is switched on, the charge is momentarily discharged through the PUT, the electrical resistance $R_2$, and the LED 11. As a result, the LED 11 emits light in a very short period of time. The LED 11 emits light at the same frequency as the frequency at which the PUT is switched on, that is to say, at the frequency of the signals obtained by modulating the signals which were output by the ion selective electrode 8. Accordingly, if the light emitted from the LED 11 is transmitted to the receiving side 2 by means of the optical fiber 3 and fed to the frequency/voltage converter 6, the output signals from the converter 6 correspond to the signals from said ion selective electrode 8, and thus, the indicating meter 7 can be actuated.

According to the above described construction, the largest part of the electrical power consumed by the transmitting side 1 is consumed by the LED 11. Provided that when the PUT is switched off, the capacitor 13 is completely charged, and when the PUT is switched on, the charge on the capacitor 13 is completely discharged through the LED 11, then the mean current i which passes through the LED 11 may be expressed by the following equation:

$$i = C(V_{B1} + V_{B2}) \cdot f$$

wherein C is the capacitance of the capacitor 13; $V_{B1}$ is the voltage of the battery $B_1$; $V_{B2}$ is the voltage of the battery $B_2$, and f is the transformed frequency of the voltage/frequency converter 10. If a 0.1 µF capacitor is selected for C, and 5 Volts selected for ($V_{B1} + V_{B2}$), and a range of from 10 to 100 Hz selected for f, then i can be reduced to a range of from 5 to 50 µA. Accordingly, if C, $V_{B1} + V_{B2}$, and f are selected as described above, the consumption of electrical power can be significantly reduced so that the transmitting side 1 can be continuously operated for about one year by four penlight batteries, IEC designation RG (size AA).

The reason why the consumption of electrical power in the transmitting side can be reduced in spite of using an LED is that the LED is not driven by the signals detected by an ion selective electrode or the output signals of a voltage/frequency converter in a different fashion from a conventional apparatus but rather is due to the fact that light is emitted from the LED by discharging current from the capacitor, the detected signals from the ion selective electrode merely serving as the trigger signal for causing the starting of the discharge of the capacitor.

Figure 2:
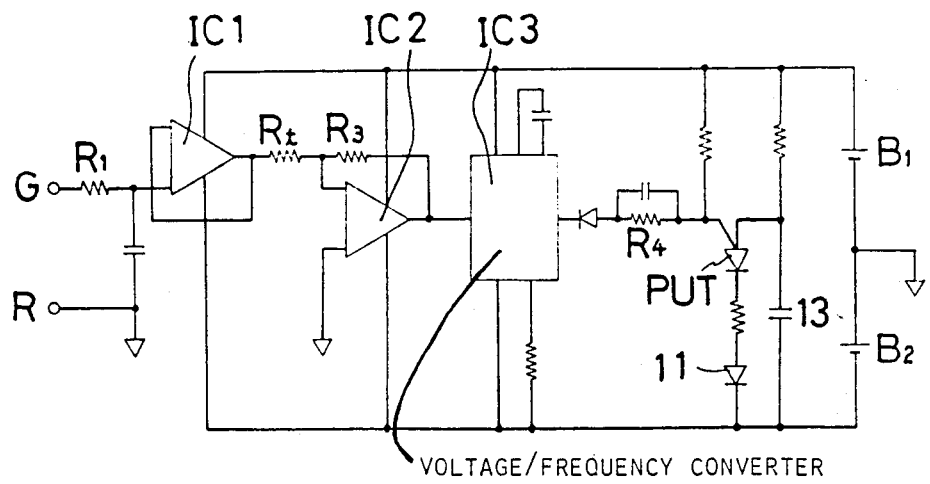
FIG. 2 is a schematic diagram of a preferred embodiment of the transmitting side circuit in the case of the invention being applied to a pH meter.
Figure 3:
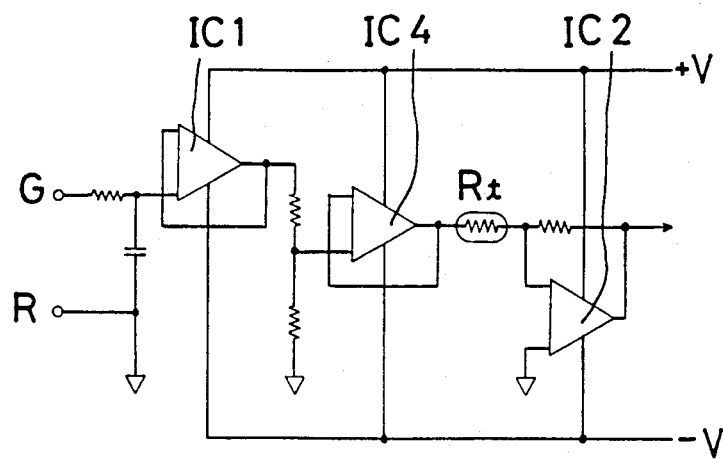
FIG. 3 is a schematic diagram of a circuit having a lower electrical power consumption than that of the circuit shown in FIG. 2.

The preferred embodiments of the present invention will now be described with reference to FIGS. 2 to 5. Referring now to FIG. 2 showing the construction of the circuit of the transmitting side in case of the invention being applied to a pH meter used as an ion-concentration measurement apparatus, G denotes a connection terminal of a glass electrode; R denotes a connection terminal of a reference electrode; $IC_1$ and $IC_2$ denote integrated circuits corresponding to the amplifier 9 shown in FIG. 1, and $IC_3$ denotes a circuit corresponding to the voltage/frequency converter 10. $R_t$ denotes a heat sensitive resistor used for temperature compensation. Although it is necessary to increase the value of resistor $R_t$ and the resistance $R_3$, which is connected in series with the resistor $R_t$, to reduce the consumption of electrical power in the amplifier 9 (comprising $IC_1$ and $IC_2$) when the resistor $R_t$ having a large resistance value is unavailable, it is only necessary to select the construction shown in FIG. 3 so as to reduce the voltage across the resistor $R_t$. That is, amplifier $IC_4$ is added between amplifiers $IC_1$ and $IC_2$ so as to reduce the voltage across resistor $R_t$.

Figure 4:
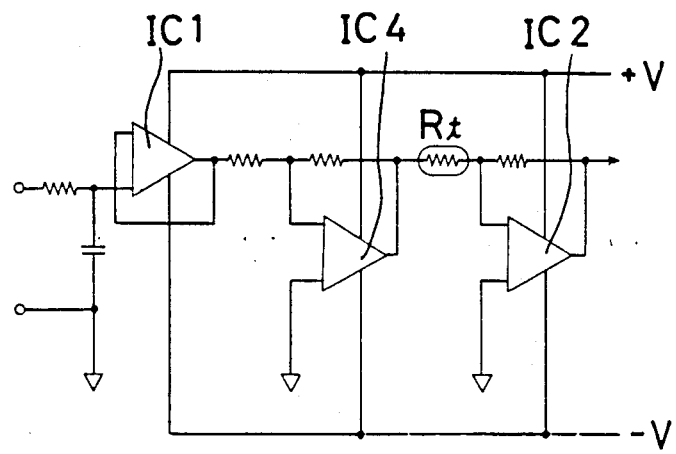
FIG. 4 is a schematic diagram of a preamplifier which may be applied to a ORP meter or anion meter.

In addition, when the present invention is applied to other apparatus, such as ORP meter and a negative ion meter, since the polarity is different from the case of a pH meter, it is only necessary to change the polarity of signals, as shown in FIG. 4. That is, the input connections of amplifier $IC_4$ are reversed.

Figure 5:
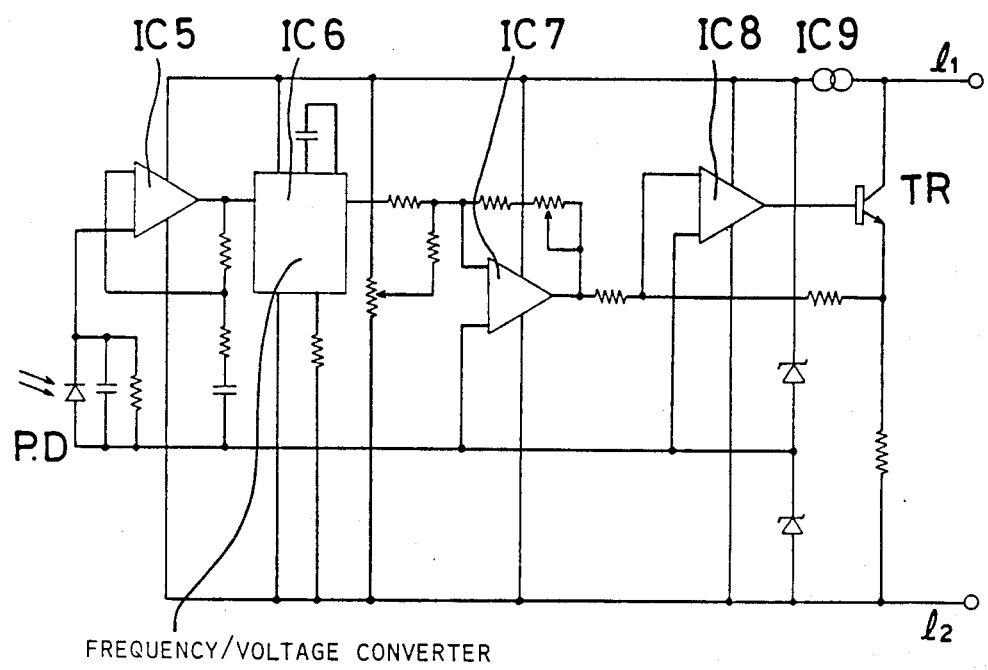
FIG. 5 is a schematic diagram of a preferred embodiment of the receiving side circuit.

Referring now to FIG. 5 showing the preferred example of the circuit of the receiving side for receiving optical signals transmitted from the transmitting side, PD denotes a photo detector; $IC_5$, $IC_7$, and $IC_8$ denote integrated circuits used as amplifiers; $IC_6$ denotes an integrated circuit used as a frequency/voltage converter, and TR denotes a transistor. The signals, which were demodulated by the frequency/voltage converter $IC_6$, are current amplified by the transistor TR, and then fed to a power supply side (not shown) through double line type transmission channels $l_1$ and $l_2$. The detailed description of this output circuit is omitted since it is comparatively familiar as a circuit for use with milliampere currents.

When an optical fiber joint type ion-concentration measurement apparatus of the present invention includes a transmitting side which is constructed as described above, it has the following effects:

The light is emitted from an LED by discharging the charge accumulated on a capacitor in a fashion which is different from that of a conventional apparatus, in which the light is emitted by the signals output by an ion selective electrode, whereby the consumption of electrical power can be significantly reduced. In particular, the suitable selection of the transformed frequency of a voltage/frequency converter, the charging voltage, and the capacitance of the capacitor leads to the possibility of using small penlight cells. Thus, the transmitting side can be very compact and lightweight and may be used for a long period of time, whereby the practical use of the apparatus becomes very high.

Although an LED emits light for only a very short time by discharging the charge on the capacitor, since the signals, which are transmitted by means of an optical fiber, are the signals which were frequency modulated by a voltage/frequency converter, that is to say, signals which transmit information stored in their frequency, the length of the light emitting time is immaterial. Thus, the detected signals can be faithfully transmitted.

I claim:

1. An optical fiber joint type ion-concentration measurement apparatus having a transmitting side in which electrical signals which are detected by an ion selective electrode are transformed into optical signals and the transformed optical signals are transmitted to a receiving side of said measurement apparatus by means of an optical fiber, wherein said transmitting side comprises:

an ion selective electrode, a voltage/frequency converter coupled to said electrode for frequency modulating signals which are detected by said ion selective electrode, a switch means coupled to said converter and switched on or off by output signals from said converter, an LED device connected in series with said switch means to form a series circuit, a charging circuit including an electrical power source and a charging-discharging capacitor having said series circuit constituting of said switch means and said LED used as a discharging circuit, wherein electrical charge which is stored in said capacitor is discharged when said switch means is switched on so as to cause said LED to emit light, and wherein the light emitted from said LED is transmitted to said receiving side by means of said optical fiber.

2. An optical fiber joint type ion-concentration measurement apparatus as set forth in claim 1, wherein said output signals from said voltage/frequency converter are fed to a control input terminal of said switch means and said charge which is discharged from said charging-discharging capacitor is fed to a controlled input terminal of said switch means.

3. An optical fiber joint type ion-concentration measurement apparatus as set forth in claim 2, wherein said switch means is switched on or off at the same frequency as that of said output signals from said voltage/frequency converter.

4. An optical fiber joint type ion-concentration measurement apparatus as set forth in claim 1, wherein said switch means is switched on or off at the same frequency as that of said output signals from said voltage/frequency converter.

* * * * *